US011877880B2

(12) United States Patent
Yang et al.

(10) Patent No.: US 11,877,880 B2
(45) Date of Patent: Jan. 23, 2024

(54) METHOD AND APPARATUS FOR CALCULATING CORONARY ARTERY CALCIUM SCORE

(71) Applicants: THE ASAN FOUNDATION, Seoul (KR); UNIVERSITY OF ULSAN FOUNDATION FOR INDUSTRY COOPERATION, Ulsan (KR)

(72) Inventors: Dong Hyun Yang, Seoul (KR); June Goo Lee, Seoul (KR); Young-Hak Kim, Seoul (KR)

(73) Assignees: THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 299 days.

(21) Appl. No.: 17/293,563

(22) PCT Filed: Nov. 7, 2019

(86) PCT No.: PCT/KR2019/015058
§ 371 (c)(1),
(2) Date: May 13, 2021

(87) PCT Pub. No.: WO2020/101264
PCT Pub. Date: May 22, 2020

(65) Prior Publication Data
US 2022/0000441 A1    Jan. 6, 2022

(30) Foreign Application Priority Data
Nov. 14, 2018    (KR) ........................ 10-2018-0140024

(51) Int. Cl.
*A61B 6/00*    (2006.01)
*G16H 50/30*    (2018.01)
(Continued)

(52) U.S. Cl.
CPC .............. *A61B 6/503* (2013.01); *A61B 6/481* (2013.01); *A61B 6/504* (2013.01); *A61B 6/5217* (2013.01);
(Continued)

(58) Field of Classification Search
CPC ......... A61B 6/503; A61B 6/481; A61B 6/504; A61B 6/5217; A61B 6/48; G06T 7/0012;
(Continued)

(56) References Cited

U.S. PATENT DOCUMENTS 8,867,822 B2    10/2014    Oh et al.
9,642,586 B2    5/2017    Kelm et al.
(Continued)

FOREIGN PATENT DOCUMENTS

CN    107016681 A    8/2017
JP    2014-534822 A    12/2014
(Continued)

OTHER PUBLICATIONS

M. Moazzam Jawaid, Panos Liatsis: "Segmentation of Soft atherosclerotic plaques using active contour models"; Nov. 2015—PhD Thesis Dept. of Electrical and Electronic Engineering; City University London. (Year: 2015).*

(Continued)

*Primary Examiner* — Siamak Harandi
(74) *Attorney, Agent, or Firm* — Oblon, McClelland, Maier & Neustadt, L.L.P.

(57) ABSTRACT

A method for calculating a coronary artery calcium score, the method comprising acquiring a target image for a coronary artery and myocardium before contrast enhancement, identifying the coronary artery included in the target image by using an artificial neural network, calculating a coronary artery calcium score based on the identified coronary artery, wherein the artificial neural network is trained (Continued)

based on a training database generated via alignment between a pre-acquired image of a coronary artery and myocardium before contrast enhancement and a pre-acquired image of a coronary artery and myocardium after contrast enhancement.

11 Claims, 4 Drawing Sheets

(51) Int. Cl.
  *G16H 50/20* (2018.01)
  *G06T 7/00* (2017.01)
(52) U.S. Cl.
  CPC ............ *G06T 7/0012* (2013.01); *G16H 50/20* (2018.01); *G16H 50/30* (2018.01); *G06T 2207/10081* (2013.01); *G06T 2207/30048* (2013.01); *G06T 2207/30101* (2013.01)
(58) Field of Classification Search
  CPC . G06T 2207/10081; G06T 2207/30048; G06T 2207/30101; G16H 50/20; G16H 50/30
  See application file for complete search history.

(56) References Cited

U.S. PATENT DOCUMENTS

| | | | |
|---|---|---|---|
| 10,452,813 B2 | 10/2019 | Sorenson et al. | |
| 2011/0243412 A1* | 10/2011 | Grass | A61B 6/504 382/131 |
| 2018/0137244 A1* | 5/2018 | Sorenson | G16H 30/20 |

FOREIGN PATENT DOCUMENTS

| | | |
|---|---|---|
| JP | 2016-41247 A | 3/2016 |
| KR | 10-2017-0021189 A | 2/2017 |
| KR | 10-1902882 B1 | 11/2018 |
| WO | WO 2018/093865 A1 | 5/2018 |

OTHER PUBLICATIONS

International Search Report dated Feb. 13, 2020 in PCT/KR2019/015058 filed Nov. 7, 2019, 2 pages.

Shadmi, R., et al., "Fully-Convolutional Deep-Learning Based System for Coronary Calcium Score Prediction From Non-Contrast Chest CT", ResearchGate, 2018, 6 total pages.

* cited by examiner

METHOD AND APPARATUS FOR CALCULATING CORONARY ARTERY CALCIUM SCORE

BACKGROUND OF THE DISCLOSURE

Field of the Disclosure

The present disclosure relates to a method and an apparatus for calculating a coronary artery calcium score by using an artificial neural network.

Related Art

Coronary artery disease is one of the causes of death, and myocardial infarction occurs in approximately 50% of people with coronary artery disease and results in death in severe cases. For the diagnosis of such coronary artery disease, there are various methods, for example, calculation of coronary artery calcium (CAC) score and coronary artery CT angiography.

Meanwhile, in the case of the coronary artery CT angiography, there is a problem in that since contrast enhancement should be performed and a patient should be thus injected with a contrast medium, an allergic reaction to the contrast medium or renal toxicity may occur. As a result, the coronary artery calcium score, which can be calculated by using CT before the contrast enhancement instead of the coronary artery CT angiography, is widely used for the diagnosis of the coronary artery disease.

Specifically, the coronary artery calcium score can be acquired through medical images such as computed tomography (CT), and can be used as a prediction factor of cardiovascular disease by quantifying the degree of calcium accumulation in blood vessels.

In order to calculate the coronary artery calcium score, there is a hassle in that a doctor or an analyst should find a coronary artery part among various organs that appear on the acquired CT and evaluate the amount of calcium in the coronary artery part. Further, in the CT before the contrast enhancement, the coronary artery part is not clearly revealed, so it is necessary to rely on the experience and judgment of the doctor or analyst, and there is a disadvantage that accuracy or objectivity is somewhat low.

PATENT DOCUMENT

Korean Patent Unexamined Publication No. 10-2014-0141526 (published on Dec. 10, 2014)

SUMMARY

A problem to be solved by the present disclosure is to provide an apparatus and a method for automatically calculating a coronary artery calcium score without intervention of a doctor or analyst by using an artificial neural network.

However, the problem to be solved by the present disclosure is not limited to the problem mentioned above, and is not mentioned, but includes an object that can be clearly understood by those skilled in the art to which the present disclosure pertains from the following description.

In accordance with one embodiment of the present disclosure, there is provided a method for calculating a coronary artery calcium score, the method comprising: acquiring a target image for a coronary artery and myocardium before contrast enhancement; identifying the coronary artery included in the target image by using an artificial neural network; and calculating a coronary artery calcium score based on the identified coronary artery, wherein the artificial neural network is trained based on a training database generated via a alignment between a pre-acquired image of a coronary artery and myocardium before contrast enhancement and a pre-acquired image of a coronary artery and myocardium after contrast enhancement.

Further, the identifying of the coronary artery may include identifying information on at least one of a left coronary artery (LCA), a left main coronary artery (LMCA), a left anterior descending coronary artery (LAD), a proximal left anterior descending artery, a middle left anterior descending artery, a distal left anterior descending artery, a right coronary artery (RCA), a proximal right coronary artery, a middle right coronary artery, a distal right coronary artery, a posterior descending artery (PDA), and myocardium in the target image by using the artificial neural network.

Further, the information may include information on at least one of a location, a shape, and a length of each of the left coronary artery, the left main coronary artery, the left anterior descending coronary artery, the proximal left anterior descending artery, the middle left anterior descending artery, the distal left anterior descending artery, the right coronary artery, the proximal right coronary artery, the middle right coronary artery, the distal right coronary artery, the posterior descending artery, and the myocardium.

Further, the calculating of the coronary artery calcium score may include identifying a calcified region in the target image, and calculating the coronary artery calcium score by using a region corresponding to the identified coronary artery in the identified region.

Further, the pre-acquired image for the coronary artery and the myocardium before the contrast enhancement and the pre-acquired image for the coronary artery and the myocardium after the contrast enhancement may be images for the same target, and the artificial neural network may include a fully convolutional network (FCN).

Further, the target image may be a computed tomography (CT) image.

In accordance with one embodiment of the present disclosure, there is provided an apparatus for calculating a coronary artery calcium score, the apparatus comprising: a target image acquisition unit acquiring a target image for a coronary artery and myocardium before contrast enhancement; a coronary artery identification unit identifying the coronary artery included in the target image by using an artificial neural network; and a calculation unit calculating a coronary artery calcium score based on the identified coronary artery, wherein the artificial neural network is trained based on a training database generated via alignment between a pre-acquired image of a coronary artery and myocardium before contrast enhancement and a pre-acquired image of a coronary artery and myocardium after contrast enhancement.

Further, the coronary artery identification unit may identify information on at least one of a left coronary artery (LCA), a left main coronary artery (LMCA), a left anterior descending coronary artery (LAD), a proximal left anterior descending artery, a middle left anterior descending artery, a distal left anterior descending artery, a right coronary artery (RCA), a proximal right coronary artery, a middle right coronary artery, a distal right coronary artery, a posterior descending artery (PDA), and myocardium in the target image by using the artificial neural network.

Further, the information may include information on at least one of a location, a shape, and a length of each of the left coronary artery, the left main coronary artery, the left anterior descending coronary artery, the proximal left anterior descending artery, the middle left anterior descending artery, the distal left anterior descending artery, the right coronary artery, the proximal right coronary artery, the middle right coronary artery, the distal right coronary artery, the posterior descending artery, and the myocardium.

Further, the calculation unit may identify a calcified region in the target image, and calculate the coronary artery calcium score by using a region corresponding to the identified coronary artery in the identified region.

Further, the pre-acquired image for the coronary artery and the myocardium before the contrast enhancement and the pre-acquired image for the coronary artery and the myocardium after the contrast enhancement may be images for the same target, and the artificial neural network may include a fully convolutional network (FCN).

Further, the target image may be a computed tomography (CT) image.

In accordance with one embodiment of the present disclosure, there is provided a computer readable recording medium storing a computer program, comprising: acquiring a target image for a coronary artery and myocardium before contrast enhancement; identifying the coronary artery included in the target image by using an artificial neural network; and calculating a coronary artery calcium score based on the identified coronary artery, wherein the artificial neural network includes a command for allowing a processor to perform a method for calculating a coronary artery calcium score in which training is performed based on a training database via alignment between a pre-acquired image of a coronary artery and myocardium before contrast enhancement and a pre-acquired image of a coronary artery and myocardium after contrast enhancement.

According to an embodiment of the present disclosure, the apparatus and the method for calculating a coronary artery calcium score identify the coronary artery by using the artificial neural network and calculate the coronary artery calcium score based on the identified coronary artery to enhance accuracy, reliability, and objectivity for the calculation of the coronary artery calcium score.

Meanwhile, effects which can be obtained in the present disclosure are not limited to the aforementioned effects and other unmentioned effects will be clearly understood by those skilled in the art to which the present disclosure pertains from the following description.

DESCRIPTION OF EXEMPLARY EMBODIMENTS

Figure 1:
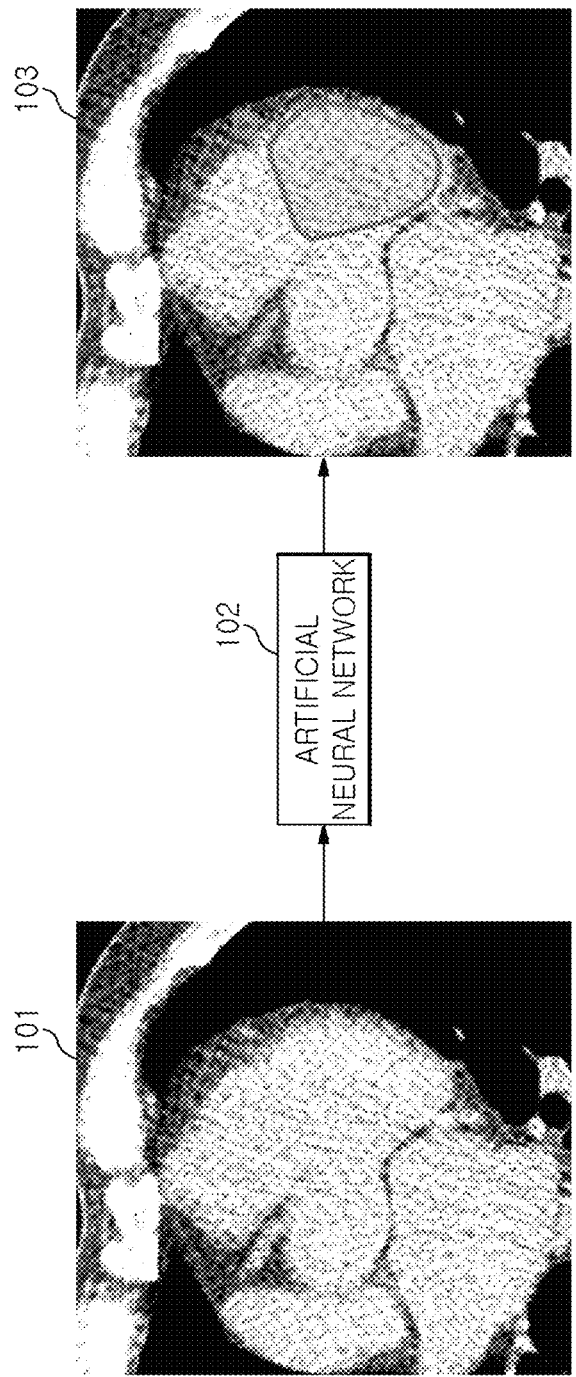
FIG. 1 illustrates an example of a coronary artery identifying process using an artificial neural network according to an embodiment of the present disclosure.

The advantages and features of the present disclosure and the methods of accomplishing these will be clearly understood from the following description taken in conjunction with the accompanying drawings. However, embodiments are not limited to those embodiments described, as embodiments may be implemented in various forms. It should be noted that the present embodiments are provided to make a full disclosure and also to allow those skilled in the art to know the full range of the embodiments. Therefore, the embodiments are to be defined only by the scope of the appended claims.

In describing the embodiments of the present disclosure, if it is determined that detailed description of related known components or functions unnecessarily obscures the gist of the present disclosure, the detailed description thereof will be omitted. Further, the terminologies to be described below are defined in consideration of functions of the embodiments of the present disclosure and may vary depending on a user's or an operator's intention or practice. Accordingly, the definition thereof may be made on a basis of the content throughout the specification.

The present disclosure may be modified and include various embodiments. Specific embodiments will be exemplarily illustrated in the drawings and described in the detailed description of the embodiments. However, it should be understood that they are not intended to limit the present disclosure to specific embodiments but rather to cover all modifications, similarities, and alternatives that are included in the spirit and scope of the present disclosure.

The terms used herein, including ordinal numbers such as "first" and "second" may be used to describe, and not to limit, various components. The terms simply distinguish the components from one another.

When it is said that a component is "connected" or "linked" to another component, it should be understood that the former component may be directly connected or linked to the latter component or a third component may be interposed between the two components.

FIG. 1 illustrates an example of a coronary artery identifying process using an artificial neural network according to an embodiment of the present disclosure.

Referring to FIG. 1, an input image 101 may be an image of a human heart region. More specifically, the input image 101 may include an image of a coronary artery and a myocardium before contrast enhancement.

An apparatus for calculating a coronary artery calcium score may allow a region of the coronary artery included in the input image 10 to be identified by an artificial neural network 102. For example, as illustrated in FIG. 1, the identified coronary artery region may be a highlighted part in the output image 103, for example, a part indicated by X, Y, or Z.

More specifically, for example, the apparatus for calculating a coronary artery calcium score may classify the coronary arteries included in the input image 101 in detail according to the types thereof, and furthermore, also classify the myocardium. The coronary arteries classified by the apparatus for calculating a coronary artery calcium score may include a left coronary artery (LCA), a left main coronary artery (LMCA), a left anterior descending coronary artery (LAD), a proximal left anterior descending artery, a middle left anterior descending artery, a distal left anterior descending artery, a right coronary artery (RCA), a proximal right coronary artery, a middle right coronary artery, a distal right coronary artery, a posterior descending artery (PDA), and the like. The myocardium classified by the apparatus for calculating a coronary artery calcium score may include, for example, a left ventricle and a right ventricle.

Figure 2:
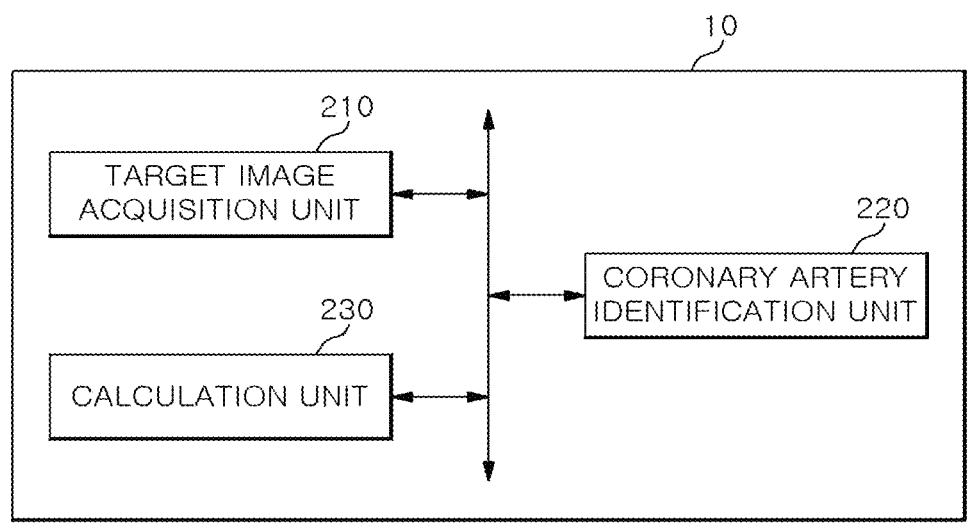
FIG. 2 illustrates an example of a functional configuration of an apparatus for calculating a coronary artery calcium score according to an embodiment of the present disclosure.

FIG. 2 illustrates an example of a functional configuration of an apparatus for calculating a coronary artery calcium score according to an embodiment of the present disclosure.

Referring to FIG. 2, the apparatus 10 for calculating a coronary artery calcium score may include a target image acquisition unit 210, a coronary artery identification unit 220, and a calculation unit 230.

The target image acquisition unit 210 may acquire a target image of the coronary and the myocardium before the contrast enhancement. The target image may include a medical image. For example, the target image may include a computed tomography (CT) image, but is not limited thereto.

In some cases, it goes without saying that the target image may include organs other than the coronary artery and the myocardium. However, since the target image is an image before a contrast medium is administered, the target image may be an image in an ambiguous state in which a boundary of each organ is not clearly revealed. A specific example related thereto may be described with reference to FIG. 4.

The coronary artery identification unit 220 may identify the coronary artery included in the target image by using the artificial neural network 102. Here, the artificial neural network 102 performs learning based on a training database generated via alignment between the pre-acquired image of the coronary artery and the myocardium before the contrast enhancement and the pre-acquired image of the coronary artery and the myocardium after the contrast enhancement.

The pre-acquired image of the coronary artery and the myocardium before the contrast enhancement and the pre-acquired image of the coronary artery and the myocardium after the contrast enhancement as an image of the same target, i.e., the same patient, may be a vast amount of data stored in advance.

Meanwhile, there may be a plurality of images before and after the contrast enhancement used for the learning of the artificial neural network 102, and the aligned images before and after the contrast enhancement may be images of the same target. The alignment of the images of the same target is easy for those skilled in the art, so a more detailed description related thereto may be omitted.

Meanwhile, based on the administration of the contrast medium to the patient, a medical image after the contrast enhancement may be acquired, and the medical image after the contrast enhancement allows each organ to be more clearly distinguished. The above-described artificial neural network 102 may be an algorithm that is learned to accurately classify each organ included in the image before the contrast enhancement when receiving the image before the contrast enhancement as an input image later by using the medical image after the contrast enhancement.

The coronary arteries may be classified according to the types in the medical image after the contrast enhancement used for the learning of the artificial neural network 102, and accordingly, the coronary arteries may be learned to be further divided into detailed types in addition to classifying the coronary artery itself.

The artificial neural network 102 may include a fully convolutional network (FCN). However, the artificial neural network 102 is not limited thereto, and may include various machine learning algorithms (or a deep learning algorithm or an artificial intelligence algorithm) related to image identification.

The coronary artery identification unit 220 may classify the myocardium and the coronary artery in the target image by using the artificial neural network 102 and further classify the coronary artery in detail according to the type. The classification may be performed based on information on at least one of a location, a shape, and a length of each of the left coronary artery, the left main coronary artery, the left anterior descending coronary artery, the proximal left anterior descending artery, the middle left anterior descending artery, the distal left anterior descending artery, the right coronary artery, the proximal right coronary artery, the middle right coronary artery, the distal right coronary artery, the posterior descending artery, and the myocardium.

The calculation unit 230 may calculate the coronary artery calcium score based on the identified coronary artery. The identification unit 230 may identify a calcified region (or a region in which calcium is accumulated) in the target image and determine a region corresponding the identified coronary artery among the identified regions. The calculation unit 230 may calculate the coronary artery calcium score according to a calcification degree of a region corresponding to the coronary artery.

More specifically, the target image may include the myocardium or other organs in addition to the coronary artery. Accordingly, when the calcified region is identified for the entire target image, there may be the calcified region in a part other than the coronary artery for various reasons. The calculation unit 230 may calculate the coronary artery calcium score by determining the region corresponding to the coronary artery in the calcified region as described above.

In this case, information on which coronary artery is calcified a lot based on the type of identified coronary artery may also be acquired. In other words, the apparatus 10 for calculating a coronary artery calcium score may perform more detailed calculation of the coronary artery calcium score, and further perform a diagnose a predicted site of cardiovascular disease, a probability of occurrence of cardiovascular disease, a risk level, etc., by using the information.

In some cases, the calculation unit 230 may first identify the region corresponding to the coronary artery in the target image and determine the calcification degree for the region, and also simultaneously identify the region corresponding to the coronary artery and determine the calcification degree, of course.

Meanwhile, the calcium score is a value which depends on an amount of accumulated calcium in the coronary artery, and the calculation unit 230 may automatically calculate the calcium score according to a preset criterion. A detailed description will be omitted because it is easy for those skilled in the art in relation to the criterion for calculating the calcium score.

Figure 3:
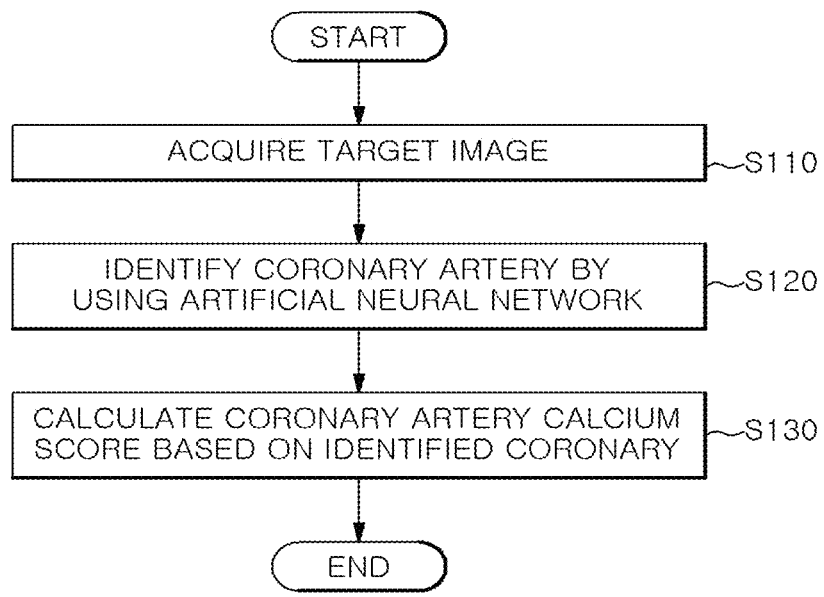
FIG. 3 illustrates a flow of each step of a method for calculating a coronary artery calcium score according to an embodiment of the present disclosure.

FIG. 3 illustrates a flow of each step of a method for calculating a coronary artery calcium score according to an embodiment of the present disclosure. Hereinafter, in FIG. 3, each component of the apparatus 10 for calculating a coronary artery calcium score of FIG. 2 will be described, and further, each step of the method illustrated in FIG. 3 may be performed in a different order illustrated in the figure in some cases, of course.

Referring to FIG. 3, a target image acquisition unit 210 may acquire a target image of a coronary artery and myocardium before contrast enhancement (S110). More specifically, the target image acquisition unit 210 may acquire, as the target image, a medical image including the coronary artery and the myocardium of a patient to which a contrast medium is not administered. The medical image may include various types of images medically used, computed tomography (CT) images, and the like.

Meanwhile, the target image acquired by the target image acquisition unit 210 as a medical image before the contrast enhancement may be generally an image in which a distinction between the coronary artery and other organs is ambiguous.

A coronary artery identification unit 220 may identify the coronary artery by using an artificial neural network 102 (S120). Specifically, the coronary artery identification unit 220 may identify the coronary artery included in the target image by using the artificial neural network 102. Further, the coronary artery identification unit 220 may use the artificial neural network 102 in order to more clearly distinguish the coronary artery in such a target image.

The artificial neural network 102 may be an algorithm learned by using a training database acquired via alignment between the image of the coronary artery and the myocardium before the contrast enhancement and the image of the coronary artery and the myocardium after the contrast enhancement. In this case, the images before and after the contrast enhancement used for the alignment may be images for the same target, i.e., the same patient. The coronary artery identification unit 220 may identify the coronary artery and the myocardium in the target image in detail based on the artificial neural network 102.

The calculation unit 230 may calculate the coronary artery calcium score based on the identified coronary artery (S130). More specifically, the calculation unit 230 may acquire information on a calcified part by determining the target image, and compare the calcified part and a part of the identified coronary artery to determine a part corresponding to the coronary in the calcified part. Based on the determination, the calculation unit 230 may calculate the coronary artery calcium score by performing an analysis of a calcification degree of the coronary artery.

In some cases, the calculation unit 230 may first identify a region corresponding to the coronary artery in the target image and determine the calcification degree for the corresponding region, or also simultaneously identify the coronary artery region and determine the calcification degree, of course.

Here, the coronary artery calcium score may be calculated by utilizing various techniques generally used. For example, the coronary artery calcium score may be calculated by using a method for measuring the amount of calcium accumulated in the coronary artery and scoring in proportion to the degree of the amount.

Figure 4:
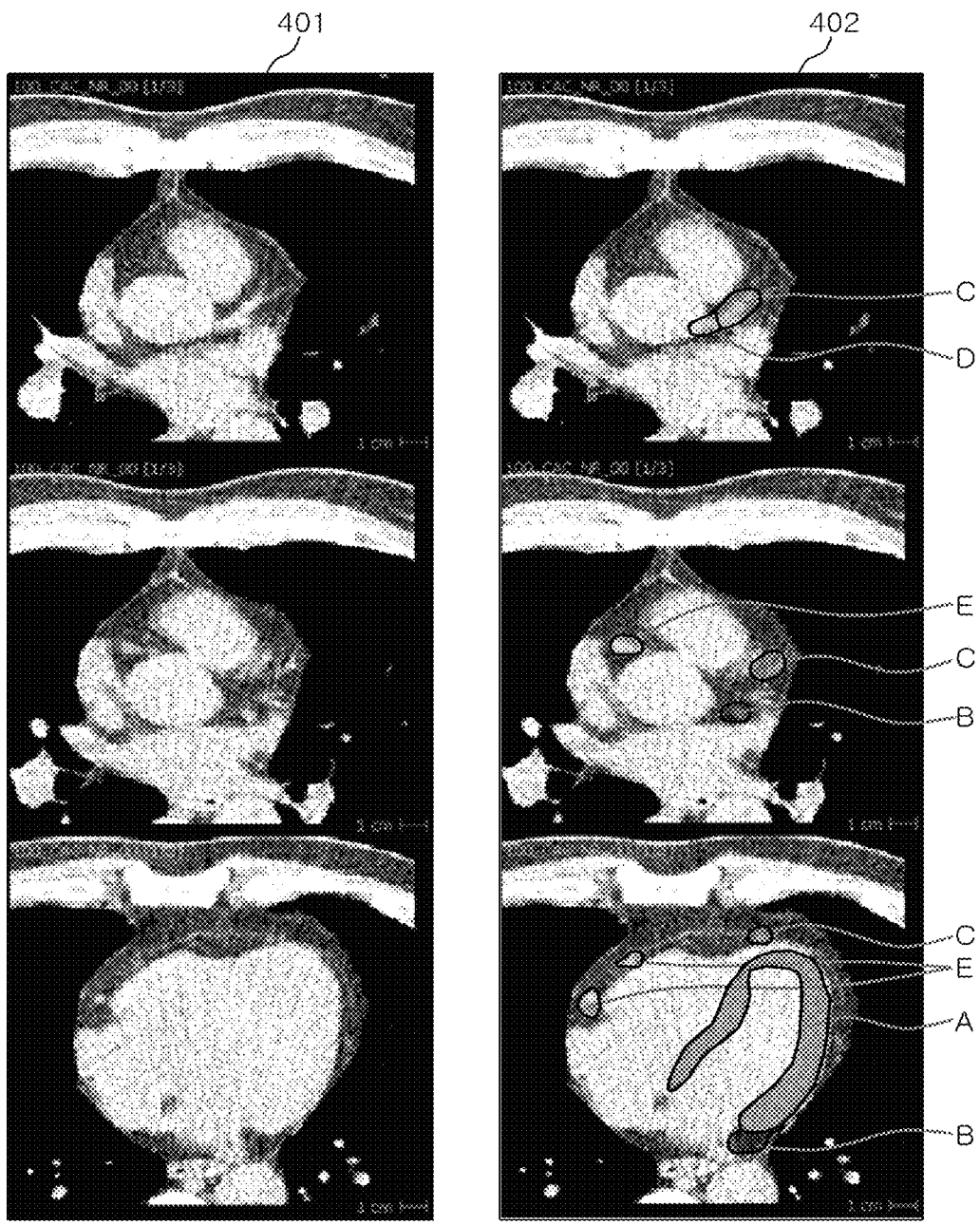
FIG. 4 illustrates examples of an input image and an output image of an apparatus for calculating a coronary artery calcium score according to an embodiment of the present disclosure.

FIG. 4 illustrates examples of an input image and an output image of an apparatus for calculating a coronary artery calcium score according to an embodiment of the present disclosure.

The apparatus 10 for calculating a coronary artery calcium score may receive an input image 401 as the target image. The apparatus 10 for calculating a coronary artery calcium score may analyze the input image 401 based on the artificial neural network 102 and provide an output image 402 in which the coronary artery and the myocardium are distinguished.

As illustrated in FIG. 4, the input image 401 as a medical image before the contrast enhancement may be an image in which the distinction of each organ appearing in the image is ambiguous. However, the part corresponding to the coronary artery may be distinguished and displayed like the output image 402 based on the input image 401 that is identified by the coronary artery identification unit 220 of the present disclosure.

A part indicated by A in the output image 402 may indicate a part corresponding to a left ventricle and other parts, e.g., parts indicated by B to E may parts corresponding to the coronary artery. As described above, the apparatus 10 for calculating a coronary artery calcium score may classify the coronary arteries in detail, so the coronary arteries may be classified and displayed according to the types as illustrated in the output image 402. However, the classification is just an example, and the spirit of the present disclosure is not limited thereto, of course.

Further, the output image 402 may be provided to be displayed in the apparatus 10 for calculating a coronary artery calcium score, and in some cases, the output image 402, is not provided and consequently, only a calcium score for each coronary artery and a final average calcium score may be calculated and provided.

The combinations of the respective blocks of a block diagram and the combinations of the respective sequences of a flow diagram attached herein may be carried out by computer program instructions. Since the computer program instructions may be executed by the processor of a general purpose computer, a special purpose computer, or other programmable data processing apparatus, the instructions, executed by the processor of the computer or other programmable data processing apparatus, create means for performing functions described in the respective sequences of the flow diagram or the respective blocks of the block diagram. The computer program instructions, in order to implement functions in a specific manner, may be stored in a computer-readable storage medium or a computer-useable storage medium for other programmable data processing apparatus, and the instructions stored in the computer-readable storage medium or the computer-useable storage medium may produce manufacturing items that include means for instructions to perform the functions described in the respective sequences of the flow diagram or the respective blocks of the block diagram. The computer program instructions may be loaded in a computer or other programmable data processing apparatus, and therefore, the instructions, which are a series of sequences executed in a computer or other programmable data processing apparatus to create processes executed by a computer to operate a computer or other programmable data processing apparatus, may provide operations for executing functions described in the respective sequences of the flow diagram or the respective blocks of the block diagram.

Moreover, the respective block or the respective sequences may refer to two or more modules, segments, or codes including at least one executable instruction for executing a specific logic function(s). In some alternative embodiments, it is noted that the functions described in the sequences may be run out of order. For example, two consecutive sequences may be executed simultaneously or in reverse order according to the particular function.

The above description illustrates the technical idea of the present invention, and it will be understood by those skilled in the art to which this present invention belongs that various changes and modifications may be made without departing from the scope of the essential characteristics of the present invention. Therefore, the exemplary embodiments disclosed herein are not used to limit the technical idea of the present invention, but to explain the present invention, and the scope of the technical idea of the present invention is not limited by those embodiments. Therefore, the scope of protection of the present invention should be construed as defined in the following claims, and all technical ideas that fall within the technical idea of the present invention are intended to be embraced by the scope of the claims of the present invention.

What is claimed is:

1. A method for calculating a coronary artery calcium score, the method comprising:
   acquiring a target image for a coronary artery and myocardium before contrast enhancement;
   identifying the coronary artery included in the target image by using an artificial neural network; and
   calculating a coronary artery calcium score based on the identified coronary artery,
   wherein the artificial neural network is trained based on a training database generated via alignment between a pre-acquired image of a coronary artery and myocardium before contrast enhancement and a pre-acquired image of a coronary artery and myocardium after contrast enhancement, and
   wherein the calculating of the coronary artery calcium score includes:
      when identifying a calcified region in the target image, identifying a first region corresponding to the identified coronary artery in the identified calcified region, and calculating the coronary artery calcium score for the first region, and
      when identifying a coronary artery region in the target image, identifying a second region corresponding to a calcified region in the identified coronary artery region, and calculating the coronary artery calcium score for the second region.

2. The method of claim 1, wherein the identifying of the coronary artery includes identifying information on at least one of a left coronary artery (LCA), a left main coronary artery (LMCA), a left anterior descending coronary artery (LAD), a proximal left anterior descending artery, a middle left anterior descending artery, a distal left anterior descending artery, a right coronary artery (RCA), a proximal right coronary artery, a middle right coronary artery, a distal right coronary artery, a posterior descending artery (PDA), and myocardium in the target image by using the artificial neural network.

3. The method of claim 2, wherein the information includes information on at least one of a location, a shape, and a length of each of the left coronary artery, the left main coronary artery, the left anterior descending coronary artery, the proximal left anterior descending artery, the middle left anterior descending artery, the distal left anterior descending artery, the right coronary artery, the proximal right coronary artery, the middle right coronary artery, the distal right coronary artery, the posterior descending artery, and the myocardium.

4. The method of claim 1, wherein the pre-acquired image for the coronary artery and the myocardium before the contrast enhancement and the pre-acquired image for the coronary artery and the myocardium after the contrast enhancement are images for the same target, and
   the artificial neural network includes a fully convolutional network (FCN).

5. The method of claim 1, wherein the target image is a computed tomography (CT) image.

6. An apparatus for calculating a coronary artery calcium score, the apparatus comprising:
   processing circuitry configured to:
      acquire a target image for a coronary artery and myocardium before contrast enhancement,
      identify the coronary artery included in the target image by using an artificial neural network, and
      calculate a coronary artery calcium score based on the identified coronary artery,
   wherein the artificial neural network is trained based on a training database generated via alignment between a pre-acquired image of a coronary artery and myocardium before contrast enhancement and a pre-acquired image of a coronary artery and myocardium after contrast enhancement, and
   wherein the processing circuitry is configured to:
      when identifying a calcified region in the target image, identify a first region corresponding to the identified coronary artery in the identified calcified region, and calculate the coronary artery calcium score for the first region, and
      when identifying a coronary artery region in the target image, identify a second region corresponding to a calcified region in the identified coronary artery region, and calculate the coronary artery calcium score for the second region.

7. The apparatus of claim 6, wherein the processing circuitry is configured to identify information on at least one of a left coronary artery (LCA), a left main coronary artery (LMCA), a left anterior descending coronary artery (LAD), a proximal left anterior descending artery, a middle left anterior descending artery, a distal left anterior descending artery, a right coronary artery (RCA), a proximal right coronary artery, a middle right coronary artery, a distal right coronary artery, a posterior descending artery (PDA), and myocardium in the target image by using the artificial neural network.

8. The apparatus of claim 7, wherein the information includes information on at least one of a location, a shape, and a length of each of the left coronary artery, the left main coronary artery, the left anterior descending coronary artery, the proximal left anterior descending artery, the middle left anterior descending artery, the distal left anterior descending artery, the right coronary artery, the proximal right coronary artery, the middle right coronary artery, the distal right coronary artery, the posterior descending artery, and the myocardium.

9. The apparatus of claim 6, wherein the pre-acquired image for the coronary artery and the myocardium before the contrast enhancement and the pre-acquired image for the coronary artery and the myocardium after the contrast enhancement are images for the same target, and
   the artificial neural network includes a fully convolutional network (FCN).

10. The apparatus of claim 6, wherein the target image is a computed tomography (CT) image.

11. A non-transitory computer readable recording medium storing a computer program, comprising:
   acquiring a target image for a coronary artery and myocardium before contrast enhancement;
   identifying the coronary artery included in the target image by using an artificial neural network; and
   calculating a coronary artery calcium score based on the identified coronary artery, wherein the artificial neural network includes a command for allowing a processor to perform a method for calculating a coronary artery calcium score in which training is performed based on a training database via alignment between a pre-acquired image of a coronary artery and myocardium before contrast enhancement and a pre-acquired image of a coronary artery and myocardium after contrast enhancement, and
   wherein the calculating of the coronary artery calcium score includes:
      when identifying a calcified region in the target image, identifying a first region corresponding to the identified coronary artery in the identified calcified region, and calculating the coronary artery calcium score for the first region, and when identifying a coronary artery region in the target image, identifying a second region corresponding to a calcified region in the identified coronary artery region, and calculating the coronary artery calcium score for the second region.

\* \* \* \* \*